US008993339B2

(12) United States Patent
Kim et al.

(10) Patent No.: US 8,993,339 B2
(45) Date of Patent: Mar. 31, 2015

(54) HYBRID NANOSTRUCTURES FOR MOLECULAR ANALYSIS (75) Inventors: Ansoon Kim, Mountain View, CA (US); Zhiyong Li, Foster City, CA (US); R Stanley Williams, Portola Valley, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 0 days.

(21) Appl. No.: 14/006,721

(22) PCT Filed: Mar. 23, 2011

(86) PCT No.: PCT/US2011/029612
§ 371 (c)(1),
(2), (4) Date: Sep. 23, 2013

(87) PCT Pub. No.: WO2012/128762
PCT Pub. Date: Sep. 27, 2012

(65) Prior Publication Data
US 2014/0024131 A1    Jan. 23, 2014

(51) Int. Cl.
*G01N 21/00* (2006.01)
*G01N 21/65* (2006.01)
*G01N 21/552* (2014.01)
*G01N 21/64* (2006.01)

(52) U.S. Cl.
CPC .............. *G01N 21/00* (2013.01); *G01N 21/554* (2013.01); *G01N 21/648* (2013.01); *G01N 21/658* (2013.01)
USPC ......................................... 436/172; 436/164

(58) Field of Classification Search
CPC .................................................. G01N 21/554

USPC ................................................... 436/172, 164
See application file for complete search history.

(56) References Cited

U.S. PATENT DOCUMENTS

| | | | |
|---|---|---|---|
| 2004/0218184 A1* | 11/2004 | Jorgenson et al. | 356/419 |
| 2006/0038990 A1* | 2/2006 | Habib et al. | 356/301 |
| 2007/0086001 A1* | 4/2007 | Islam et al. | 356/301 |
| 2008/0149479 A1 | 6/2008 | Olofsson | |
| 2009/0032781 A1 | 2/2009 | Wang et al. | |
| 2009/0101996 A1 | 4/2009 | Bradley et al. | |
| 2010/0080899 A1 | 4/2010 | Mao et al. | |

(Continued)

FOREIGN PATENT DOCUMENTS

EP        0675411 A1    10/1995

OTHER PUBLICATIONS

Wei Wu, Min Hu, Fung Suong Ou, Zhiyong Li, and, R Stanley Williams, Cones fabricated by 3D nanoimprint lithography for highly sensitive surface enhanced Raman spectroscopy, Nanotechnology 21 (2010) 255502 (p. 1-6).*

(Continued)

*Primary Examiner* — Christopher A Hixson
*Assistant Examiner* — Emily Berkeley
(74) *Attorney, Agent, or Firm* — Hewlett-Packard Patent Department (57) ABSTRACT

A hybrid nanostructure for molecular analysis is disclosed. The structure includes a plurality of nanofingers wherein each nanofinger is coated with a metal coating, is attached at one end to a substrate, and is freely bendable along its length such that the second ends of each nanofinger are capable of movement toward each other to form a cavity. The structure further includes a nanoparticle trapped in the cavity. An array of hybrid nanostructures and a method for fabricating the hybrid nanostructures are also disclosed.

9 Claims, 12 Drawing Sheets

(56) References Cited

U.S. PATENT DOCUMENTS

2010/0183875 A1 7/2010 Mao
2010/0193768 A1 8/2010 Habib

OTHER PUBLICATIONS

Bezryadin, A., et al., "Electrostatic trapping of single conducting nanoparticles between nanoelectrodes." Applied Physics Letters, vol. 71, No. 9 (1997), pp. 1273-1275.

Hu, Min et al., 'Gold Nanofingers for Molecule Trapping and Detection', Journal of American Chemical Society, vol. 132, DOI: 10.1021/ja105248h, pp. 12820-12822, Aug. 26, 2010.

Lim, Dong-Kwon, et al., "Nanogap-engineerable Raman-active nanodumbbells for single-molecule detection." Nature materials, vol. 9, No. 1 (2009): pp. 60-67.

International Search Report, Korean IPO, Jan. 10, 2012, PCT Patent Application No. PCT/US2011/029612.

\* cited by examiner

HYBRID NANOSTRUCTURES FOR MOLECULAR ANALYSIS

STATEMENT OF GOVERNMENT INTEREST

This invention was made with government support under Contract No. HR0011-09-3-0002, awarded by Defense Advanced Research Projects Agency. The government has certain rights in the invention.

BACKGROUND

Examples of the present invention relate generally to systems for performing molecular analysis, such as surface-enhanced Raman spectroscopy (SERS), enhanced fluorescence, enhanced luminescence, and plasmonic sensing, among other systems.

With specific regard to SERS, Raman spectroscopy is a spectroscopic technique used in condensed matter physics and chemistry to study vibrational, rotational, and other low-frequency modes in molecular systems. In a Raman spectroscopic experiment, an approximately monochromatic beam of light of a particular wavelength range passes through a sample of molecules and a spectrum of scattered light is emitted. The spectrum of wavelengths emitted from the molecule is called a "Raman spectrum" and the emitted light is called "Raman scattered light." A Raman spectrum can reveal electronic, vibrational, and rotational energy levels of a molecule. Different molecules produce different Raman spectra that can be used like fingerprints to identify molecules and even to determine the structure of molecules.

Raman spectroscopy is used to study the transitions between molecular energy states when photons interact with molecules, which results in the energy of the scattered photons being shifted. The Raman scattering of a molecule can be seen as two processes. The molecule, which is at a certain energy state, is first excited into another (either virtual or real) energy state by the incident photons, which is ordinarily in the optical frequency domain. The excited molecule then radiates as a dipole source under the influence of the environment in which it sits, at a frequency that may be lower (i.e., Stokes scattering) or that may be higher anti-Stokes scattering) compared to the excitation photons. The Raman spectrum of different molecules or species (such as virus encapsulations) has characteristic peaks that can be used to identify the species. Accordingly, Raman spectroscopy is a useful technique in a variety of chemical or biological sensing and identification applications. However, the intrinsic Raman scattering process is very inefficient, and rough metal surfaces, various types of nano-antennas, as well as waveguiding structures have been used to enhance the Raman scattering processes (i.e., the excitation and/or radiation processes described above).

The Raman scattered light generated by molecules or species adsorbed on or within a few nanometers of a structured metal surface can be $10^3$ to $10^{14}$ times greater than the Raman scattered light generated by the same species in solution or in the gas phase. This scattering cross section amplification process is called surface-enhanced Raman spectroscopy ("SERS"). In recent years, SERS has emerged as a routine and powerful tool for investigating molecular structures and characterizing interfacial and thin-film systems, even enabling single-molecule detection. Engineers, physicists, and chemists continue to seek improvements in systems and methods for performing SERS.

BRIEF DESCRIPTION OF THE DRAWINGS

The detailed description will make reference to the following drawings, in which like reference numerals may correspond to similar, though perhaps not identical, components. For the sake of brevity, reference numerals having a previously described function may or may not be described in connection with other drawings in which they appear.

DETAILED DESCRIPTION

Reference is now made in detail to specific examples of the disclosed hybrid nanostructure and specific examples of ways for creating the disclosed hybrid nanostructures. When applicable, alternative examples are also briefly described.

It is noted that, as used in this specification and the appended claims, the singular forms "a," "an," and "the" include plural referents unless the context clearly dictates otherwise.

As used in this specification and the appended claims, "about" means a ±10% variance caused by, for example, variations in manufacturing processes.

Additionally, this discussion has been presented in terms of SERS analysis for the sake of convenience. However, it is noted that the same hybrid nanostructures can be employed in other analytical techniques, including, but not limited to, enhanced fluorescence, enhanced luminescence, plasmonic sensing, optical scattering, or absorption.

A new class of rationally engineered SERS structures is disclosed, including a plurality of nanofingers, pillar or pole-like structures that can undergo a self-closing process when exposed to micro-capillary forces, and at least one nanoparticle, which can become trapped in the cavity formed between the nanofingers after they have undergone self-closing. These hybrid nanostructures can be mass fabricated by first using 3-D imprinting methods or roll-to-roll processes to create the nanofingers and then exposing the nanofingers to a nanoparticle dispersion. An array of groups of these hybrid nanostructures may also be fabricated.

Identifying the optimal, rationally engineered nanostructure for SERS applications and finding an easy way to manufacture them has always been an important goal for researchers in the field of chemical or biological sensing. In the past, bottom-up synthesized nanocrystals of various shapes, such as wires, cubes, multi-pods, stars, core-shells, or bowties, and top-down fabricated nanostructures, such as nanocones, nanograss, or grating/antenna hybrid structures, have been extensively studied. However, the top-down fabrication method has high overhead costs and requires the use of heavy and expensive equipment with inflexible critical dimensions. Additionally, the bottom-up method relies on natural assembly processes such as chemical bonding, which can be hard to control, particularly in the fabrication of structures with complex geometries such as the hybrid nanostructures described herein.

SERS nanostructures including a plurality of nanofingers and at least one analyte have also been studied. In these nanostructures, the nanofingers also undergo a self-closing process, during which at least one analyte becomes trapped in the "gaps" between the nanofingers, or where the bent nanofingers come close to each other. For these nanostructures to be useful in sensing applications, it is important that the presence of analytes or other molecules on the nanofingers be easily detectable. Therefore, in order to maximize detectability in sensing applications, nanostructures that are capable of amplifying the intensity of the Raman signals of analytes and other target molecules or allowing detection of analytes and other target molecules in alternative ways have been studied.

The hybrid nanostructure disclosed herein includes a plurality of nanofingers and at least one nanoparticle. The nanoparticle can enhance the intensity of the Raman signals of target molecules on the nanostructures used in SERS applications and can facilitate the use of an alternative sensing method for detecting certain target molecules. Additionally, the hybrid nanostructure can be easily mass-manufactured in a variety of different geometries that include different sized nanoparticles.

Figure 1:
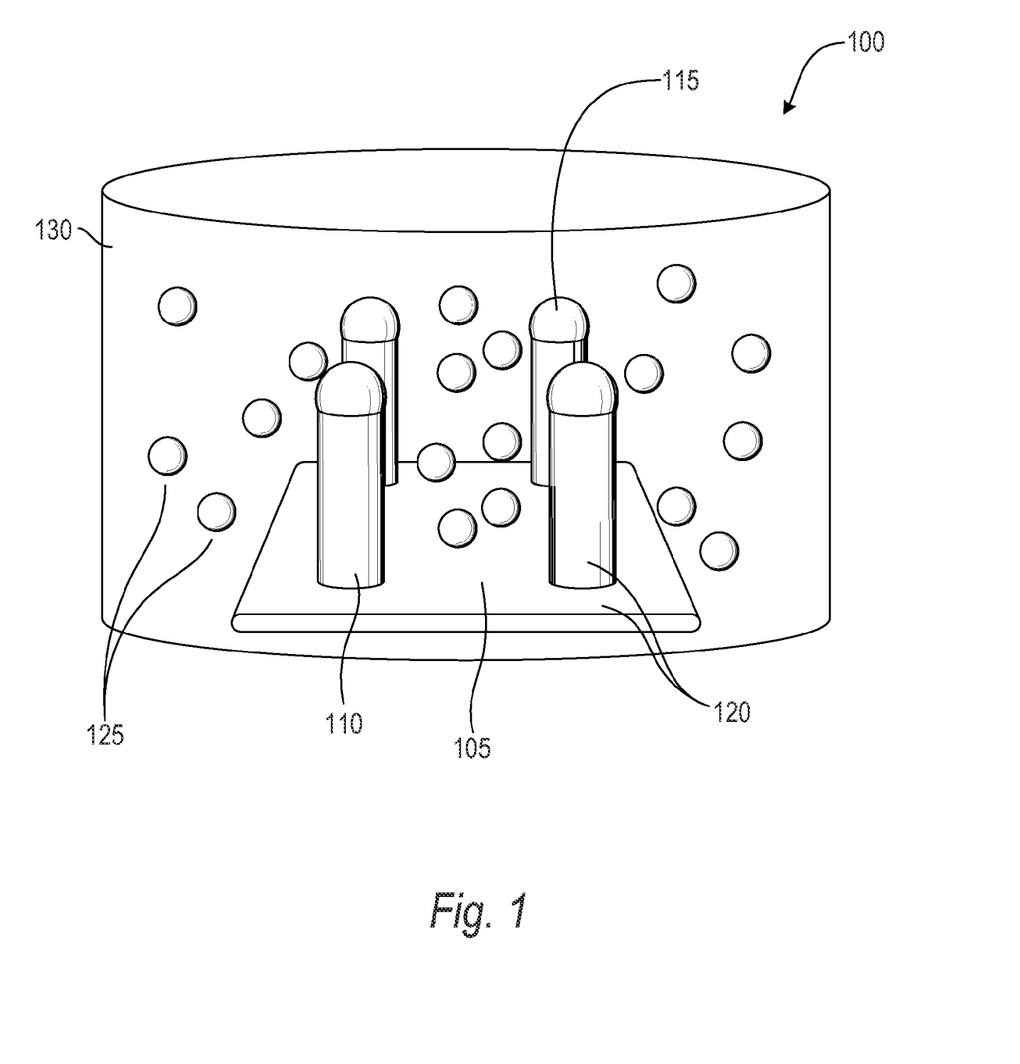
FIG. 1 depicts an example nanostructure including four nanofingers capped by metal tips and immersed in a dispersion of nanoparticles.

FIG. 1 depicts an example nanostructure including four nanofingers immersed in a dispersion of nanoparticles 100. The nanostructure 120, including metal-coated, bendable nanofingers 110 attached to a substrate 105, may be fabricated using a variety of methods.

In one example, a method of fabricating nanofingers 110 on a substrate 105 may include first designing the desired pattern of nanofingers 110 on a mold using methods such as e-beam lithography, photolithography, laser interference lithography, Focused on Beam (FIB), or self-assembly of spheres. Then, the pattern may be transferred onto silicon, glass, or another suitable substrate. In some examples, suitable polymer substrates may include polyimide, polycarbonate, or polydimethylsiloxane (PDMS).

Next, the nanofingers 110 may be fabricated using a number of different methods such as 3-D imprinting methods, embossing, chemical vapor deposition (CVD) growth, etching, or roll-to-roll processes. In some examples, the nanofingers 110 may be fabricated from one or more organic materials, Using organic materials may render the nanofingers 110 sufficiently flexible such that the neighboring nanofinger tips 115 can bend toward each other. In some examples, the nanofingers 110 may include one or more monomers, oligomers, or polymers of thermoplastic or ultraviolet (UV) curable materials, such as photoresist, polycarbonate, PDMS, polymethyl methacrylate (PMMA), or nanoimprint resist. In one example, each nanofinger 110 in a single hybrid nanostructure may include the same composition of organic materials. In other examples, the nanofingers 110 in a single hybrid nanostructure need not include the same composition of organic materials.

Alternatively, the nanofingers 110 may be fabricated using one or more flexible inorganic materials. In some examples, suitable inorganic materials may include silicon oxide, silicon, silicon nitride, alumina, diamond, diamond-like carbon, aluminum, copper, or other like materials. In one example, each nanofinger 110 in a single hybrid nanostructure (as depicted in FIGS. 2A-2D) may include the same composition of inorganic materials. In other examples, the nanofingers 110 in a single hybrid nanostructure need not include the same composition of inorganic materials.

In some examples, the height of the nanofingers 110 may range from about 50 nm to 2 μm, and the diameter may range from about 10 nm to 1 μm. Additionally, in some examples, the nanofingers 110 may be spaced apart at the base (the end of the nanofinger attached to the substrate) by a distance ranging from about 10 to 500 nm. The cross-section of the nanofingers 110 at the base may take on a variety of different shapes including circles or non-symmetrical shapes, such as ovoids.

Next, the nanofingers 110 may be coated with various types of SERS-active material which support "tense" surface plasmons, such as noble metals or aluminum. "Intense" as used herein means that the magnitude of the surface electromagnetic field generated by incident light on the nanofingers 110 is at least 100 times greater when the SERS-active material is present than when the SERS-active material is absent. In some examples, the nanofingers 110 may be coated with aluminum, gold, silver, copper, platinum, or an alloy thereof. The metal may be coated over the entire nanofinger 110 or it may be selectively coated on the nanofinger tips 115. The nanofinger 110 may also be coated with multiple layers of metals or metal alloys. In some examples, the nanofinger 110 may be coated with a 10 to 100 nm thick layer of silver metal with a 1 to 50 nm gold metal over-coating. In other examples, the nanofinger 110 may be coated with a 10 to 100 nm thick layer of gold metal with a 1 to 50 nm silver metal over-coating. In some examples, the nanofinger 110 may be further coated with a thin dielectric layer, which may serve as a functional coat capable of selectively trapping and sensing analytes or other molecules.

In some examples, analytes may be introduced to a nanostructure 120 including nanofingers 110 having a functional coat. In these examples, while the analytes may be trapped anywhere on the nanostructure 120, the analytes are much more likely to be trapped around the nanofinger tips 115 due to the surface plasmon effect, which tends to concentrate the analytes at the nanofinger tips 115 under laser Illumination. Additionally, if only the nanofinger tips 115 are coated with SERS-active metal or metals, as discussed above, the analytes will also mainly be drawn to the nanofinger tips 115.

After the nanostructure 120, including the metal-coated nanofingers 110 and substrate 105, as described above, has been fabricated, the hybrid nanostructure 200-215, as depicted in FIGS. 2A-2D, can be formed by exposing the nanostructure to nanoparticles dispersed in a dispersion medium 130.

In some examples, the nanoparticles 125 may include one or more metallic semiconducting materials and may have a diameter ranging from a few sub-nanometers to hundreds of nanometers. In some examples, quantum dots that are 5 to 20 nm in diameter may be used. Some examples of quantum dots include cadmium selenide (CdSe), cadmium telluride (CdTe), cadmium sulfide (CdS), cadmium selenide sulfide (CdSeS), cadmium telluride sulfide (CdTeS), indium arsenide (InAs), indium phosphide RIP zinc selenide (ZnSe), zinc sulfide (ZnS or any combination thereof.

In some examples, the nanoparticles 125 may be further functionalized to allow the specific binding of particular target molecules. In one example, the target molecules are analytes. Accordingly, the nanoparticles 125 may be capable of capturing the analytes from a dispersion and bringing the analytes to the surface of the nanofingers for sensing.

The nanoparticles 125 may be dispersed in the dispersion medium 130 before being exposed to the nanostructure 120, The dispersion medium 130 used may vary depending on the composition of the nanoparticles 125. However, the choice of the dispersion medium 130 is not important, so long as the nanoparticles 125 can be dispersed in it. In one example, if the nanoparticles 125 are composed of gold, the dispersion medium 130 used may be water or DMSO. In another example, gold nanoparticles may be dispersed in alcohols. In yet another example, if the nanoparticles 125 are composed of quantum dots, the dispersion medium 130 used may be water.

FIGS. 2A-2D are perspective views that depict examples of hybrid nanostructures 200, 205, 210, 215. As seen in FIGS. 2A-2D, the example hybrid nanostructures 200, 205, 210, 215 each may include a plurality of nanofingers 110 that are attached at one end to a substrate 105 and bend toward each other to create a teepee-like shape at their tips 115. The empty space in the center of the bent nanofinger tips 115 is known as a cavity 325 (as shown in FIG. 3A, a top plan view that depicts an example hybrid nanostructure).

Figure 2A:
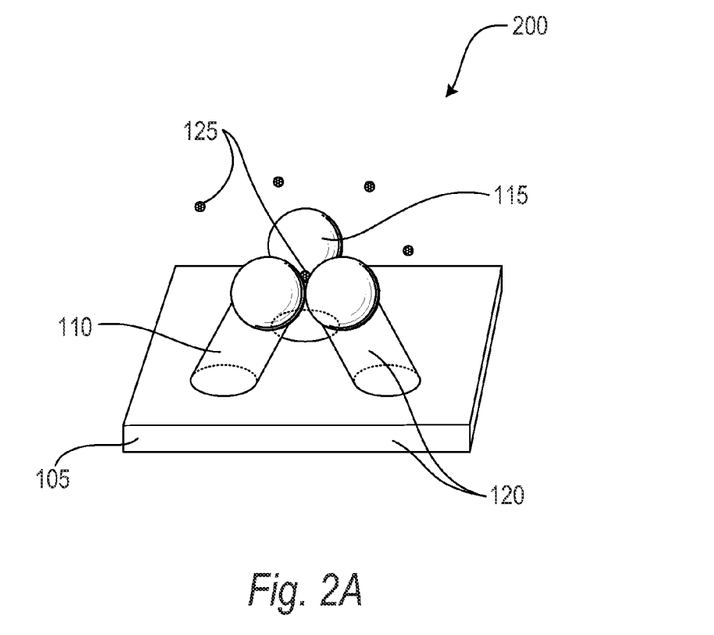
FIGS. 2A-2D are perspective views that depict a variety of example hybrid nanostructures as described herein.
Figure 2B:
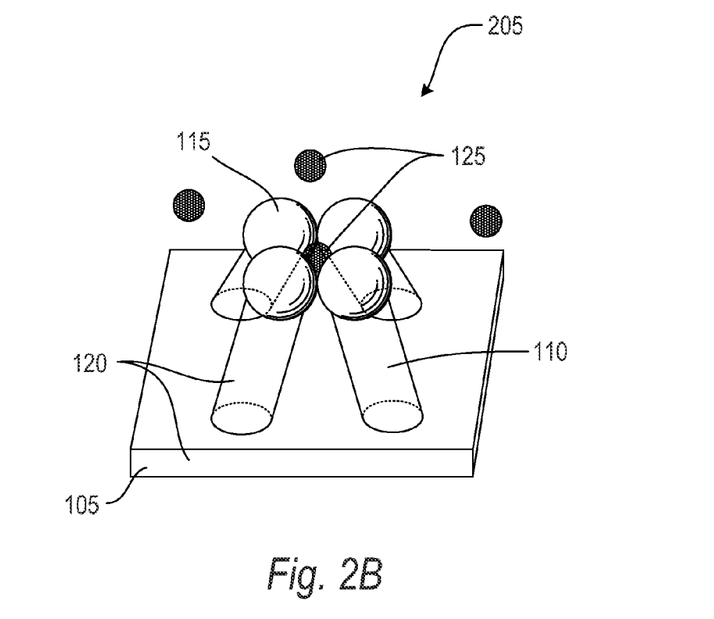
Figure 2C:
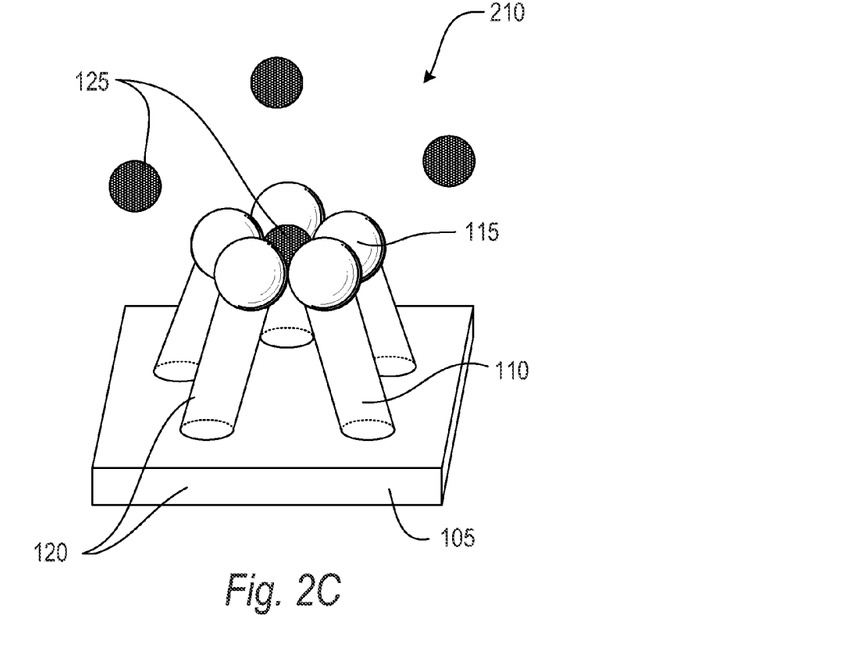

More specifically, FIG. 2A shows an example hybrid nanostructure 200 including three nanofingers 110, bent at their tips 115 to form a teepee-like shape, and a trapped nanoparticle 125. Likewise, FIG. 2B shows an example hybrid nanostructure 205 including four nanofingers 110, bent at their tips 115 to form a teepee-like shape, and a trapped nanoparticle 125; FIG. 2C shows an example hybrid nanostructure 210 including five nanofingers 110, bent at their tips 115 to form a teepee-like shape, and a trapped nanoparticle 125; and FIG. 20 shows an example hybrid nanostructure 215 including six nanofingers 110, bent at their tips 115 to form a teepee-like shape, and a trapped nanoparticle 125.

These example hybrid nanostructures 200, 205, 210, 215 may be formed when a nanostructure 120 is exposed to the dispersed nanoparticles 125. After exposure, the dispersion medium 130 may be removed and the nanostructure 120 may be dried, triggering a self-closing process. In some examples, the nanostructure 120 may be air dried. In other examples, the nanostructure 120 may be dried by other methods, including heating the nanostructure 120, pumping most of the dispersion medium 130 out and allowing the remainder of the dispersion medium 130 to evaporate, and blowing gas, such as nitrogen gas, over the nanostructure 120.

During this drying process, the nanostructure 120 may undergo self-closing. During self-closing, micro-capillary forces may cause the nanofinger tips 115 to bend towards each other at an angle, forming a teepee-like structure at the tips 115 with an empty space, known as a cavity 325, in the middle of the nanofinger tips 115. In other examples, methods such as e-beam, ion-beam or the electric charge effect or magnetic force or mechanic agitation effect may be used to induce self-closing.

In some examples, during self-closing, nanoparticles 125, as discussed above, may become trapped in the cavity 325 formed in the middle of the nanofinger tips 115. In some examples, smaller nanoparticles 125 may facilitate formation of hybrid nanostructures with fewer nanofingers 110 because geometries with less nanofingers 110 have smaller cavities 325 that can trap smaller nanoparticles 125. In other examples, larger nanoparticles 125 may facilitate formation of hybrid nanostructures with more nanofingers 110 because geometries with more nanofingers 110 have larger cavities 325 that can trap larger nanoparticles 125. However, the nanoparticle 125 need not be in the exact same shape and size as the cavity 325; the nanoparticle 125 only needs to be similar in shape and size.

Figure 2D:
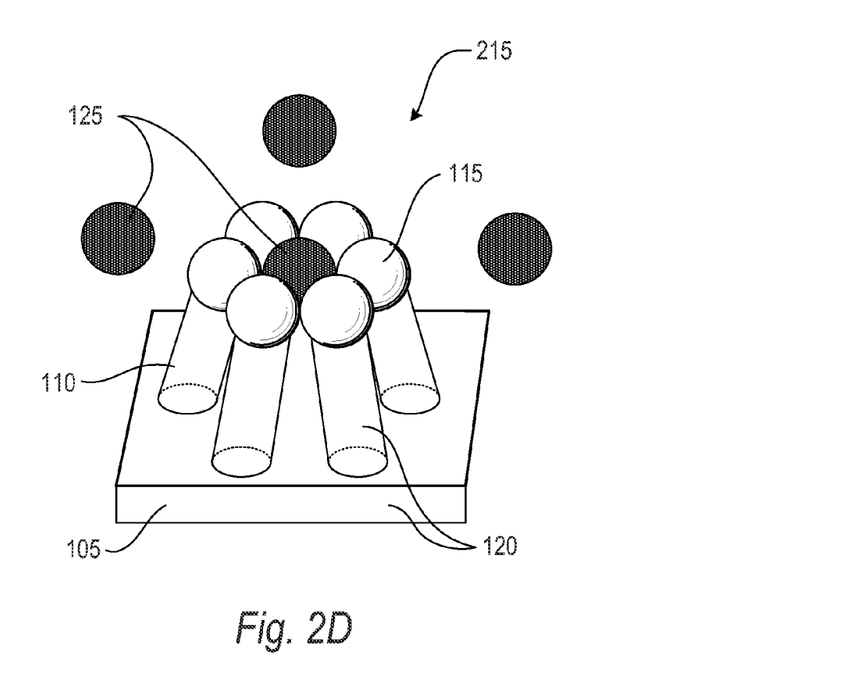
Figure 3A:
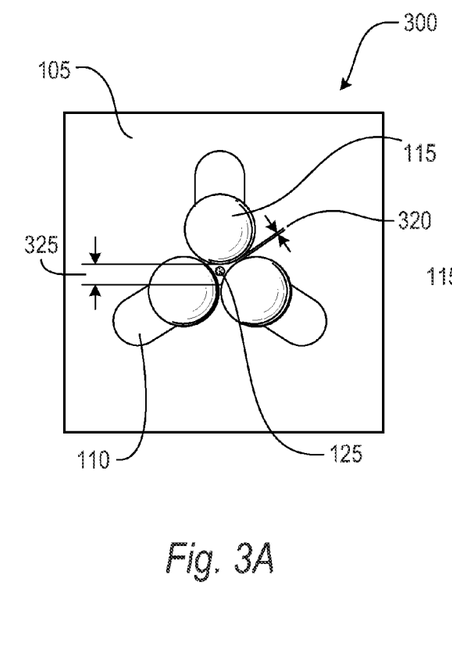
FIGS. 3A-3D are top plan views that depict a variety of example hybrid nanostructures as described herein and viewed from above.
Figure 3B:
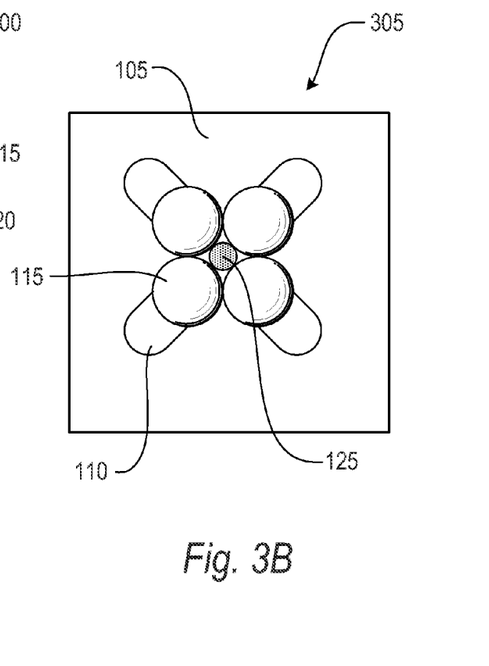

It is noted that the arrangements depicted in FIGS. 2A-20 are examples only, and other configurations of nanofingers 110, including configurations with a different number of nanofingers 110, may be employed. As discussed above and as can be seen in FIGS. 2A-2B, after self-closing, fewer nanofingers 110 in a hybrid nanostructure result in a geometry with a smaller cavity 325, suitable for trapping smaller nanoparticles 125. Likewise, as can be seen in FIGS. 2C-2D, after self-closing, more nanofingers 110 in a hybrid nanostructure result in a geometry with a larger cavity 325, suitable for trapping larger nanoparticles 125.

In some examples, the formation of hybrid nanostructures may be permanent and may rely on van der Waals interactions to hold the nanofingers 110 together at their tips 115. In other examples, the formation of the hybrid nanostructures may be reversible. For example, using a repelling electromagnetic force, mechanical force, or electric charge may open the nanofinger tips 115 back up, such that the nanofingers 110 revert to their original vertical, free-standing state.

Figures 3C, 3D:
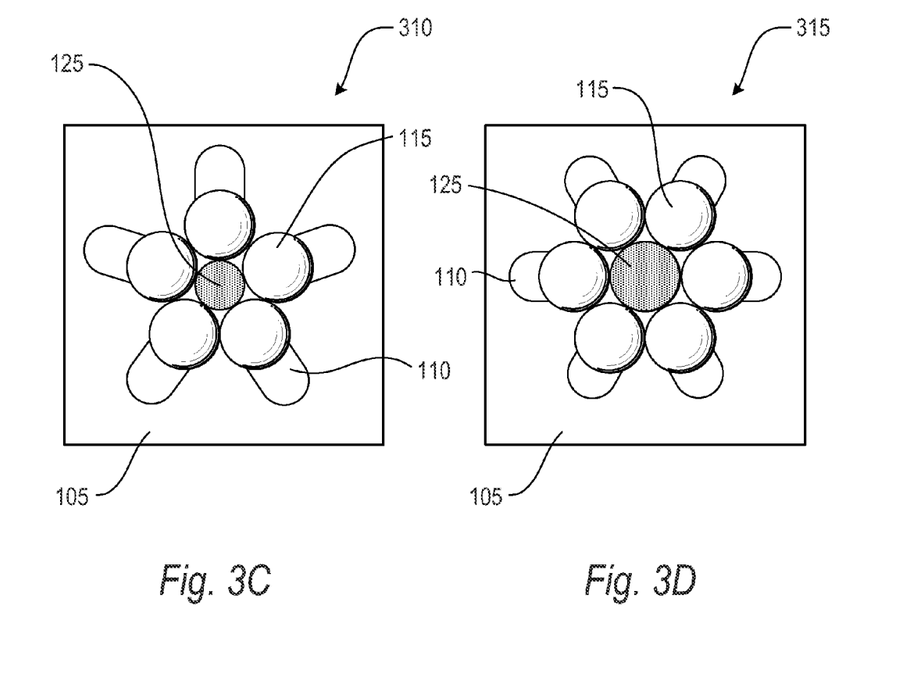

FIGS. 3A-3D are top plan views that depict a variety of examples of hybrid nanostructures 300, 305, 310, 315, as described herein. FIG. 3A shows an example hybrid nanofinger 300 including three nanofingers 110, bent at their tips to form a teepee-like shape, and a trapped nanoparticle 125. Likewise, FIG. 313 shows an example hybrid nanofinger 305 including four nanofingers 110, bent at their tips to form a teepee-like shape, and a trapped nanoparticle. 125; FIG. 30 shows an example hybrid nanofinger 310 including five nanofingers 110 bent at their tips to form a teepee-like shape and a trapped nanoparticle 125; and FIG. 3D shows an example hybrid nanofinger 315 including six nanofingers 110, bent at their tips to form a teepee-like shape, and a trapped nanoparticle 125.

As seen in FIGS. 2A-2D and FIGS. 3A-3D, as the number of nanofingers 110 increases, different arrangements, such as a polygonal arrangement of nanofingers 110, may be employed, so long as the nanofinger tips 115 in the particular arrangement all bend toward each other such that they almost touch, separated by only a small "finger gap" 320 (as shown in FIG. 3A). In some examples, the nanofinger tips 115 may be separated by a finger gap 320 of only 0.5 to 1 nm.

In some examples, there may be an enhanced electromagnetic field formed in the finger gaps 320. The magnitude of the enhancement of the electromagnetic field may depend on the size of the finger gap 320. As the size of the finger gap 320 decreases, the electromagnetic field may increase. For example, the electromagnetic field may increase in strength by 1,000 times as the finger gap 320 is decreased from 10 nm to less than 1 nm between two nanofinger tips 115. Since the SERS effect is a function of the 4th power of electromagnetic field enhancement, an increase in electromagnetic field strength by $10^3$ as the finger gap 320 decreases may result in a $10^{12}$ improvement in Raman signal strength.

In some examples, the size of the nanoparticle used in the formulation of a hybrid nanostructure may control the size of the finger gaps 320 on a nanometer scale, affecting the electromagnetic field formed in the finger gaps 320 as well.

In other examples, the finger gaps 320 between the nanofinger tips 115 may be further fine-tuned by heating processes, such as thermal heating or heating under a laser at a particular wavelength or pulse. In one example, the nanostructure 120 includes two nanofingers 110 composed of rubber and separated at the tips 115 by 10 nm. Because rubber has a linear thermal expansion of $\sim 10^{-4}/C.°$ at 20° C., if the nanofingers 110 are heated from 20° C. to 120° C., the finger gap 320 or separation between the nanofinger tips 115 may be decreased to 1 nm.

Figure 4A:
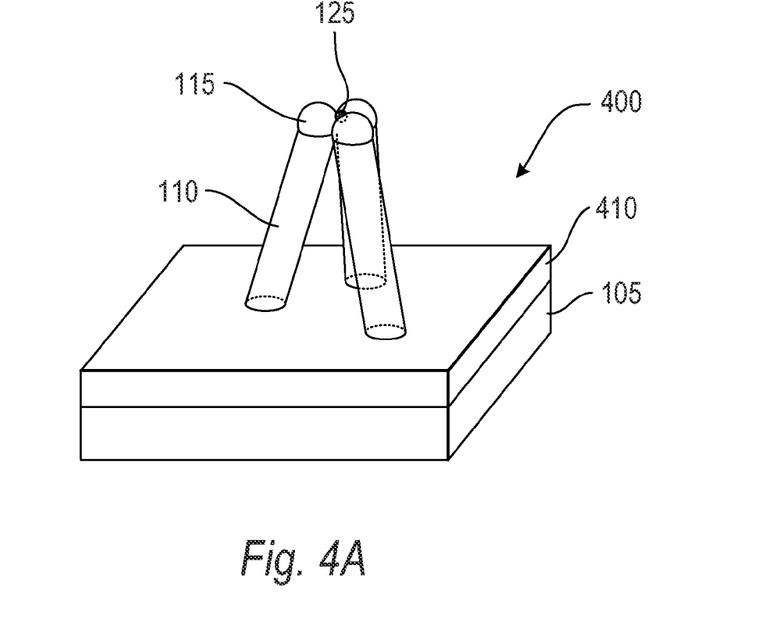
FIGS. 4A-4B are perspective views that depict examples of integrated structures combining hybrid nanostructures, as described herein, with other optics.
Figure 4B:
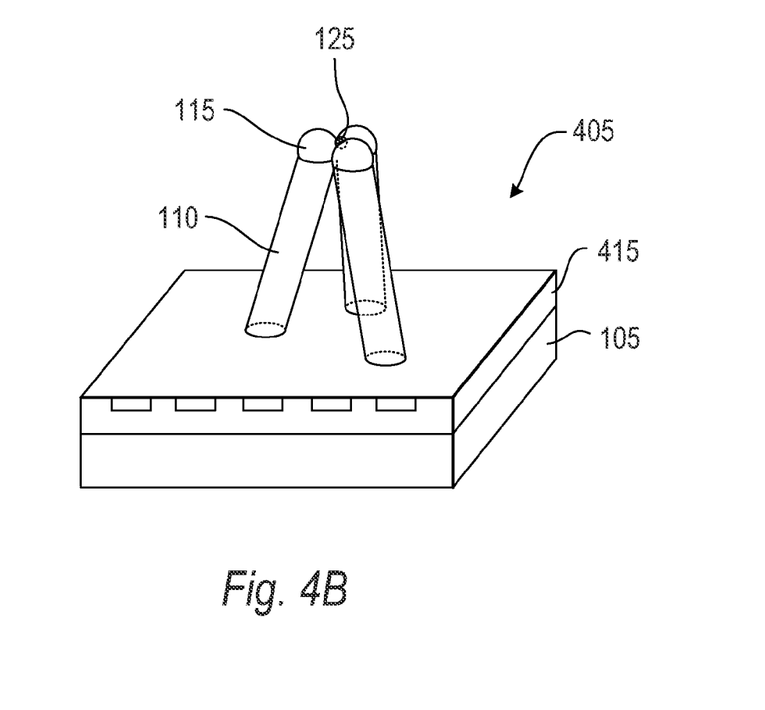

FIGS. 4A-4B are perspective views that depict examples of integrated structures 400, 405 combining hybrid nanostructures, as described herein, with other optics. FIG. 4A depicts an example hybrid nanostructure 400, including three nanofingers 110, formed on a metal mirror 410. The metal mirror 410 is in turn formed on a substrate 105. In some examples, the metal mirror 410 may be flat. In other examples, it may be concave. The metal mirror 410 may be used to reflect light into the hybrid nanostructure 400 which may increase the intensity of the hybrid nanostructure's 400 signal strength.

FIG. 4B depicts an example hybrid nanostructure 410, including three nanofingers 110, formed on a grating structure 415. The grating structure 415 is in turn formed on substrate 105. In one example, a grating structure is a periodical structure with a refractive index greater than the refractive index of air. Grating structures in conjunction with SERS structures have been discussed elsewhere, such as in U.S. Pat. Nos. 7,639,355 and 7,474,396. In another example, the hybrid nanostructure 410 itself may be used as a grating. By properly designing the pitch of the teepee structure along either one dimension or two dimensions on the substrate surface 105, an amplitude modulated interference grating can be established.

Figure 5A:
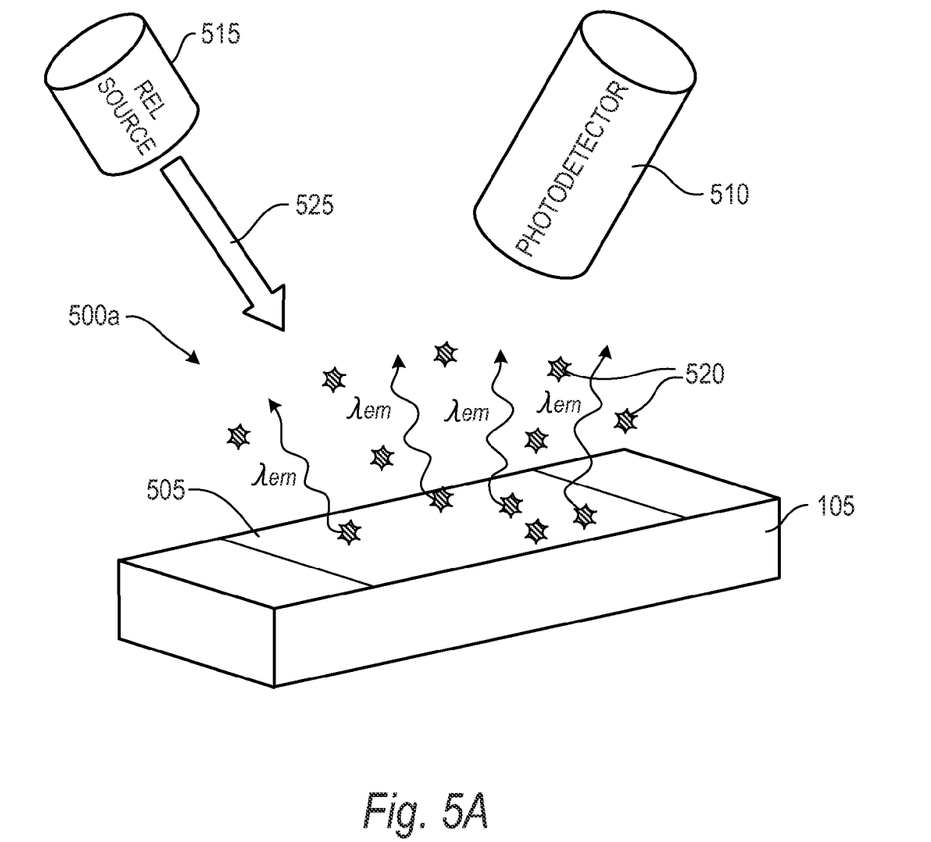
FIGS. 5A-5B each depict a schematic view of an example sensing apparatus that includes hybrid nanostructures, as described herein.
Figure 5B:
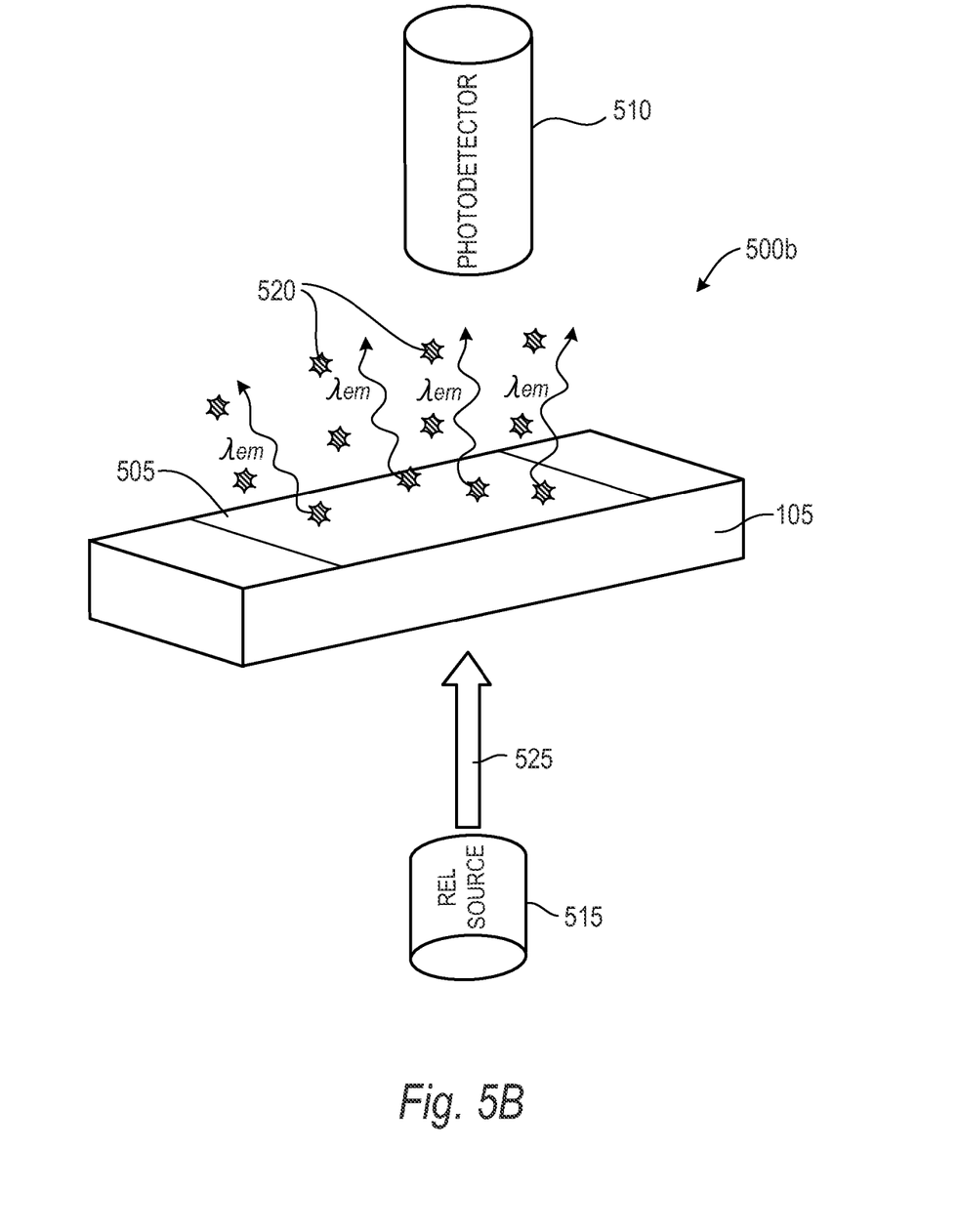

FIGS. 5A-5B each depict a schematic view of example sensing apparatuses 500a, 500b that includes hybrid nanostructures 510, as described herein. FIG. 5A shows an example of an integrated sensor 500a including a Raman-active substrate 105, an array of hybrid nanostructures 505 including a target-linked nanoparticle as described herein, a photodetector 510, a Raman-excitation light source (REL) 515, and analytes 520 to be bonded to the hybrid nanostructures 505. In the example apparatus 500a depicted in FIG. 5A, the light source 515 is positioned so that Raman-excitation light 525 shines directly on the hybrid nanostructures 505, causing the analytes 520 to undergo excitation, followed by radiation emission $\lambda_{em}$.

In another example, FIG. 5B shows an example integrated sensor 500b including the same elements as FIG. 5A. However, in FIG. 5B, the light source 515 of the example integrated sensor 500b is positioned beneath the Raman-active substrate 105 such that the Raman-excitation light passes through the substrate 105. In one example, the Raman-active substrate 105 may be transparent to the incident light.

In both example integrated sensors 500a-500b, the photodetector 510 is positioned to capture at least a portion of the Raman scattered light $\lambda_{em}$ emitted by the analytes 520 interacting with the target-linked nanoparticles in the hybrid nanostructures 505 on the surface of the Raman-active substrate 105.

The intensity of the Raman scattered light may be enhanced as a result of two mechanisms associated with the Raman-active material. First, an enhanced electromagnetic field may be produced at the nanofinger tips on the Raman-active substrate. In one example, conduction electrons in the metal surfaces of the nanofingers may enter an extended surface excited electronic state called a "surface plasmon polariton" or "localized surface plasmon." This state may be caused by the interactions between the analytes on the surface of the hybrid nanostructure and the nanofingers. The intensity of the surface plasmon polariton resonance may depend on a variety of factors, including the composition of the metal coating on the nanofingers, the size and the shape of the nanofingers, and the separation distance between the nanofingers. Second, charge transfer may occur as a result of the formation of a charge-transfer complex between the surfaces of the nanofingers and the analytes. In some examples, the electronic transitions of the charge transfer complexes are visible in the range of the electromagnetic spectrum.

Figure 6A:
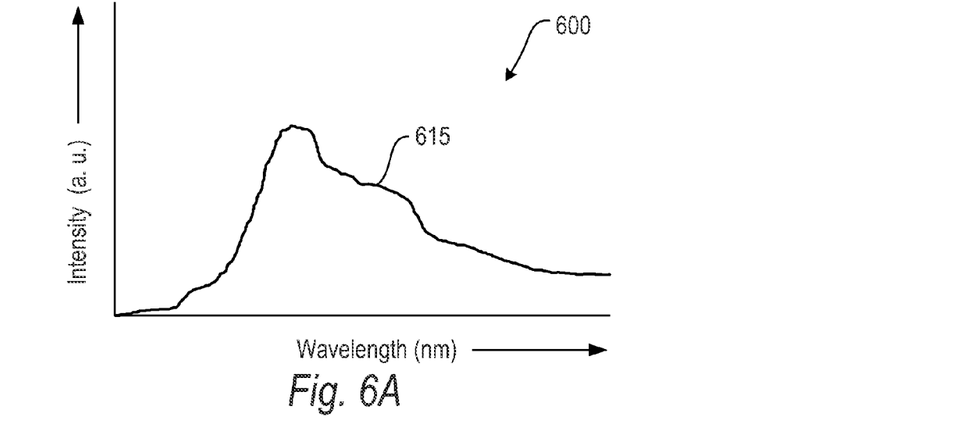
FIGS. 6A-6C, on coordinates of intensity (arbitrary units or a.u.) and wavelength (nm), are representative optical scattering spectra depicting the plasmonic resonance from, respectively, an array of nanostructures, an array of nanostructures including analytes, and an array of hybrid nanostructures including a target-linked nanoparticle and analytes.
Figure 6B:
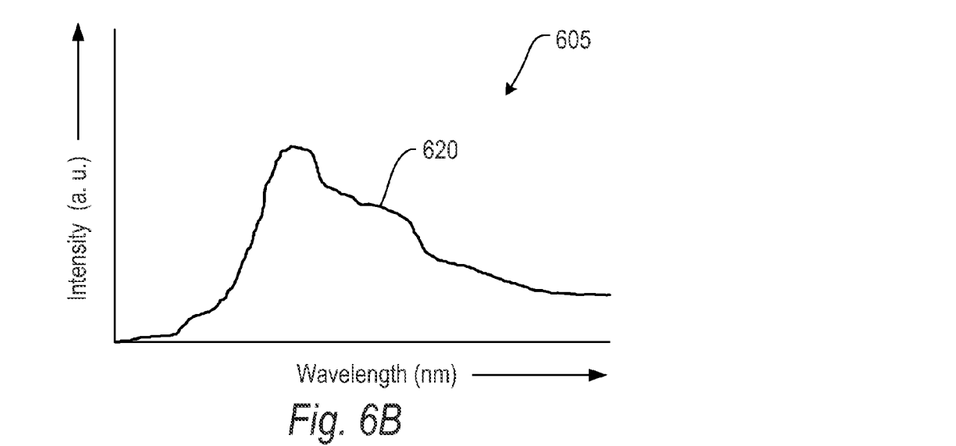
Figure 6C:
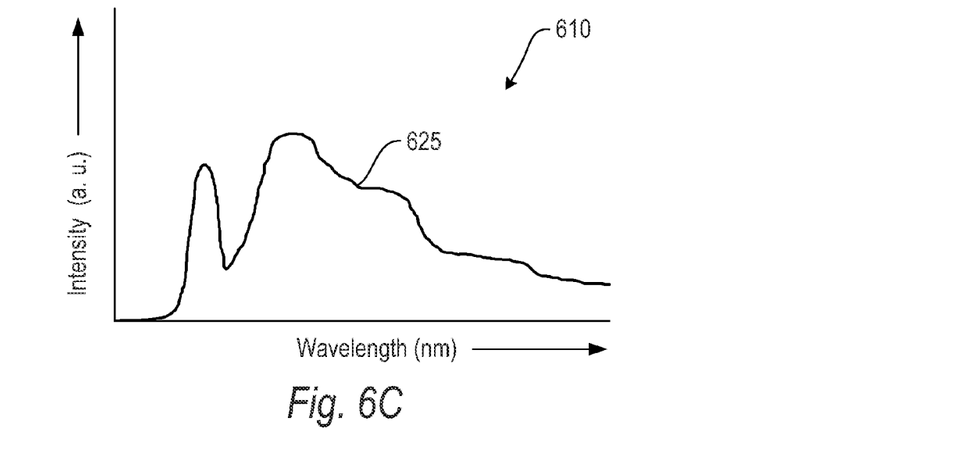

FIGS. 6A-6C, on coordinates of intensity (arbitrary units or a.u.) and wavelength (nm), are representative optical scattering spectra depicting the plasmonic resonance from, respectively, an array of nanostructures, an array of nanostructures including analytes, and an array of hybrid nanostructures including a target-linked nanoparticle and analytes, all as described herein. FIG. 6A is a representative optical scattering spectrum of an array of nanostructures with open nanofingers. FIG. 6B is a representative optical scattering spectrum of an array of nanostructures with open nanofingers including analytes. FIG. 6C is a representative optical scattering spectrum of an array of hybrid nanostructures with dosed nanofingers including a target-finked nanoparticle and analytes.

As seen in FIGS. 6A-6B, a representative optical scattering spectrum of an array of nanostructures with open nanofingers 600 and a representative optical scattering spectrum of an array of nanostructures with open nanofingers including analytes 605 appear very similar. There is virtually no difference between the two plasmonic resonance curves 615, 620. Accordingly, it appears that the presence of analytes in the nanostructure is undetectable using optical scattering if the nanostructure is not a hybrid nanostructure including a nanoparticle. As seen in FIG. 6C, a representative optical scattering spectrum of an array of hybrid nanostructures with dosed nanofingers including a target-linked nanoparticle and analytes, the presence of a target-linked nanoparticle will alter the plasmonic resonance curve 625, creating two peaks. Because target-linked nanoparticles may bind with analytes, as further discussed above, using optical scattering spectra to determine the presence of those nanoparticles can indirectly determine the presence of analytes.

Figure 7A:
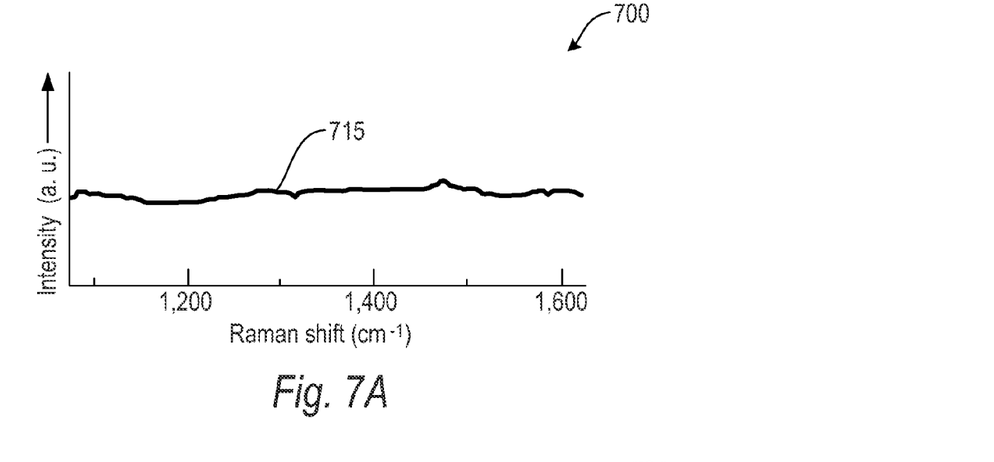
FIGS. 7A-7C, on coordinates of intensity in arbitrary units a.u. and Raman shift ($cm^{-1}$), are representative Raman spectra depicting the intensity of signals from, respectively, an array of nanostructures, an array of nanostructures including analytes, and an array of hybrid nanostructures including a target-linked nanoparticle and analytes.
Figure 7B:
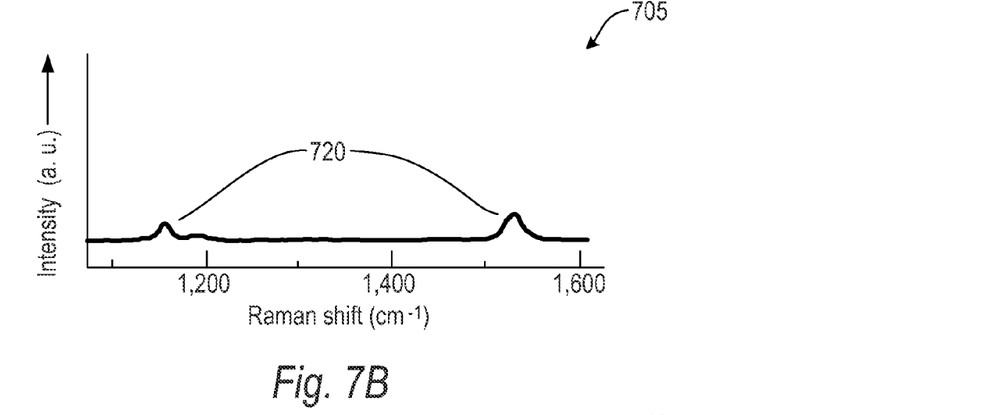
Figure 7C:
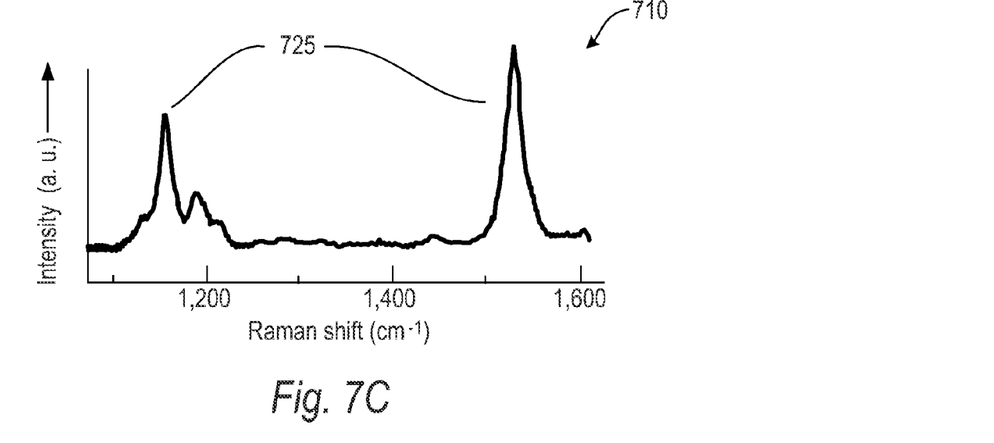

FIGS. 7A-7C, on coordinates of intensity in arbitrary units (a.u.) and Raman shift ($cm^{-1}$), are representative Raman spectra depicting the intensity of signals from, respectively, an array of nanostructures, an array of nanostructures including analytes, and an array of hybrid nanostructures including a target-linked nanoparticle and analytes, all as described herein. FIG. 7A is a representative Raman spectrum for an array of nanostructures with open nanofingers. FIG. 7B is a representative Raman spectrum for an array of nanostructures with open nanofingers including analytes. FIG. 7C is a representative Raman spectrum for an array of hybrid nanostructures with closed nanofingers including a target-linked nanoparticle and analytes.

As can be seen from comparing FIG. 7A and FIG. 7B, representative Raman spectra of an array of nanostructures with open nanofingers 700 and an array of nanostructures with open nanofingers including analytes 705, the analytes will cause two small resonance peaks in the Raman spectra 720. As can be seen from FIG. 7C, the representative Raman spectrum for an array of hybrid nanostructures with closed nanofingers including a target-linked nanoparticle and analytes 710, the presence of a target-linked nanoparticle greatly amplifies the intensity of the signal that the analytes give off. In other words, the resonance peaks of the analytes 720 from nanostructures without a target-linked nanoparticle are much smaller than the resonance peaks of the analytes 725 from hybrid nanostructures with a target-linked nanoparticle. In one example, in sensing applications, having amplified resonance peaks may allow for easier and more accurate detection of analytes and other molecules bonded to a hybrid nanostructure.

The foregoing discussion has been presented in terms of symmetrical nanostructures and symmetrical hybrid nanostructures for the sake of convenience. It should be appreciated that nanostructures and hybrid nanostructures may also be asymmetrical or less-symmetrical. Asymmetrical or less-symmetrical nanostructures and asymmetrical or less-symmetrical hybrid nanostructures are structures that lack inversion, rotational or mirror plane symmetry. In some examples, these asymmetrical or less-symmetrical nanostructures and asymmetrical or less-symmetrical hybrid nanostructures are formed naturally during the self-closing process, as described herein. In other words, during the self-closing process, the polygon shapes that are formed by the leaning nanofingers may sometimes be asymmetrical, less symmetrical, or symmetrical. A hybrid nanostructure is asymmetrical when there is a complete lack of any symmetrical elements in the structure, including an inversion center, a rotation axis, and a mirror plane. Less-symmetry (or low symmetry) is relative with respect to high symmetry. A hybrid nanostructure with less-symmetry is a hybrid nanostructure including only a subset of the symmetrical elements present in a hybrid nanostructure with high symmetry.

In some examples, the lack of symmetry in hybrid nanostructures may result in an improvement of the electromagnetic field distribution in these structures, which in turn, may result in an improvement in the SERS performance of the structures. In one example, the Raman signal from analytes on an asymmetrical hybrid nanostructure may be greater than the Raman signal from analytes on a symmetrical hybrid nanostructure. Likewise, the Raman signal from analytes on a less-symmetrical hybrid nanostructure may be greater than the Raman signal from analytes on a symmetrical hybrid nanostructure.

Figure 8A:
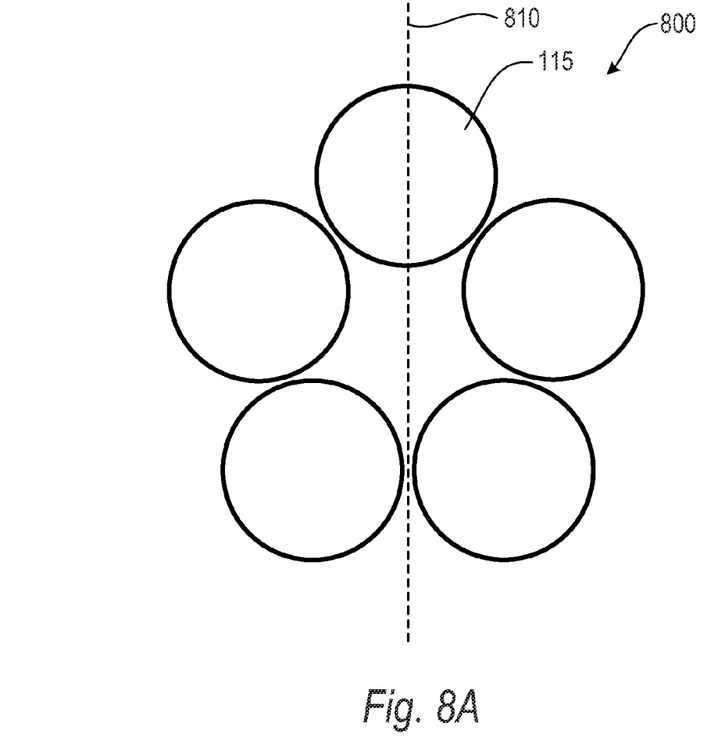
FIGS. 8A-8B are top plan views that depict, respectively, an example symmetrical nanostructure and an example asymmetrical nanostructure, as described herein but without supporting structures, wherein the lack of symmetry of the example asymmetrical nanostructure is due to a lack of mirror plane symmetry.
Figure 8B:
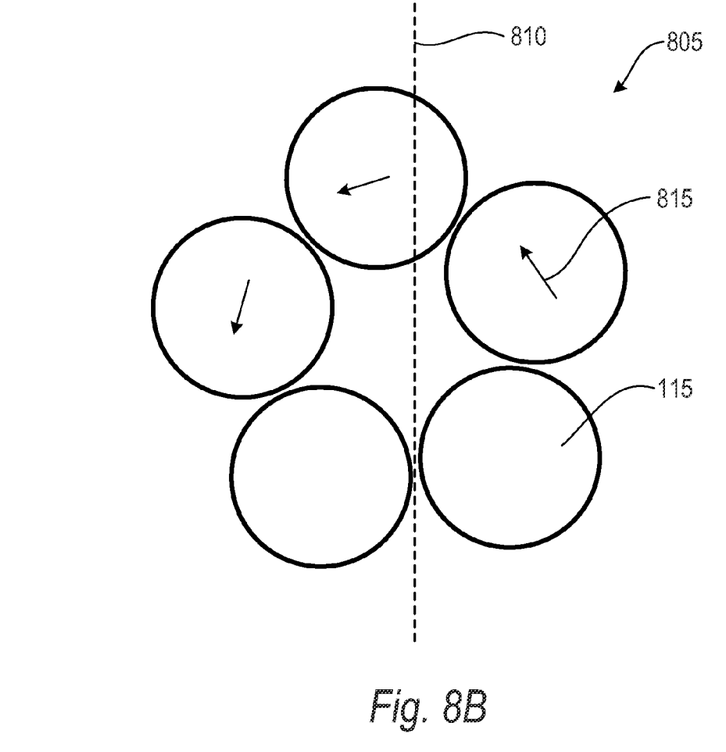

FIGS. 8A-8B are top plan views that depict, respectively, an example symmetrical nanostructure and an example asymmetrical nanostructure, as described herein but without supporting structures, wherein the lack of symmetry of the example asymmetrical nanostructure is due to a lack of mirror plane symmetry. FIG. 8A is an example of a symmetrical nanostructure 800 including five nanofingers 115. As seen in FIG. 8A, a mirror plane of symmetry 810 can be drawn down the center of the nanostructure 800. In contrast, FIG. 8B is an example of an asymmetrical nanostructure 805 including five nanofingers 115. As seen in FIG. 8B, a mirror plane of symmetry 810 cannot be drawn down the center of the nanostructure 805, and the nanostructure 805 appears to be twisted 815 in a counterclockwise direction resulting in a break of mirror plane symmetry. In other examples, the nanostructure may be twisted in a clockwise direction.

Figure 9A:
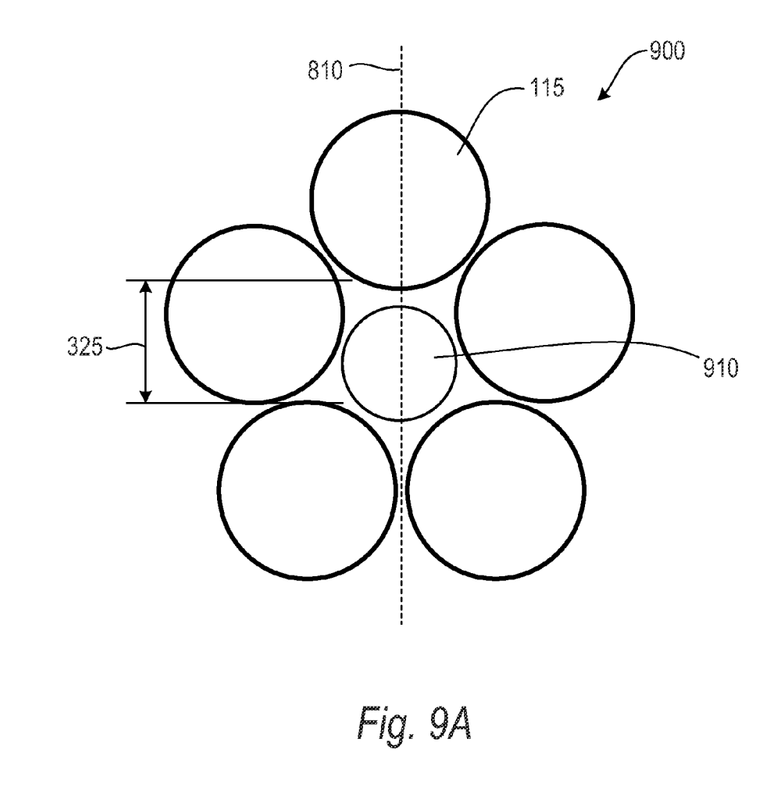
FIGS. 9A-9B are top plan views that depict, respectively, an example symmetrical hybrid nanostructure and an example asymmetrical hybrid nanostructure, as described herein but without supporting structures, wherein the lack of symmetry of the example asymmetrical hybrid nanostructure is based on the off-center position of the trapped nanoparticle.
Figure 9B:
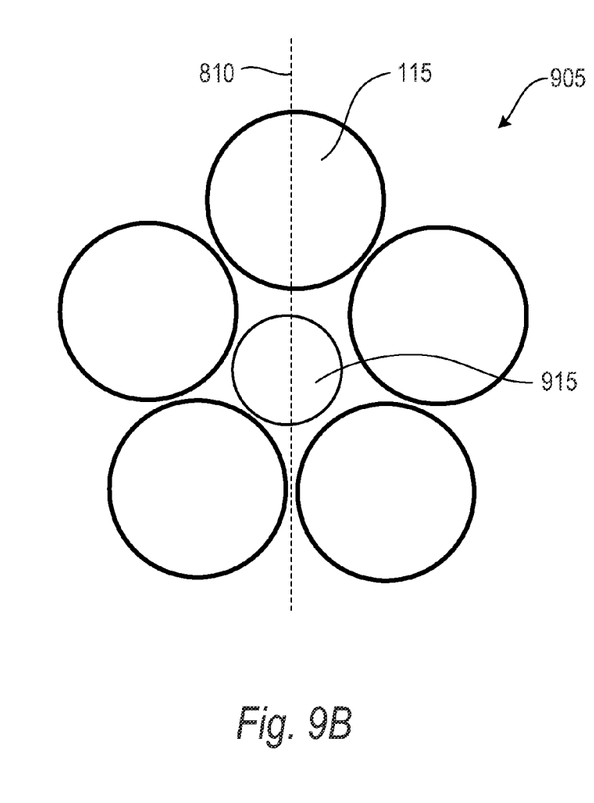

FIGS. 9A-9B are top plan views that depict, respectively, an example symmetrical hybrid nanostructure and an example asymmetrical hybrid nanostructure, as described herein but without supporting structures, wherein the lack of symmetry of the example asymmetrical hybrid nanostructure is based on the position of the trapped nanoparticle. FIG. 9A is an example of a symmetrical hybrid nanostructure 900 including five nanofingers 115 and a nanoparticle 910 positioned in the center of the cavity 325. As seen in FIG. 9A, a mirror plane of symmetry 810 can be drawn down the center of the nanostructure 900. In contrast, FIG. 9B is an example of an asymmetrical hybrid nanostructure 905 including five nanofingers 115 and a trapped nanoparticle 915 not positioned in the center of the cavity 325. As seen in FIG. 9B, a mirror plane of symmetry 810 cannot be drawn down the center of the nanostructure 905.

Figure 10A:
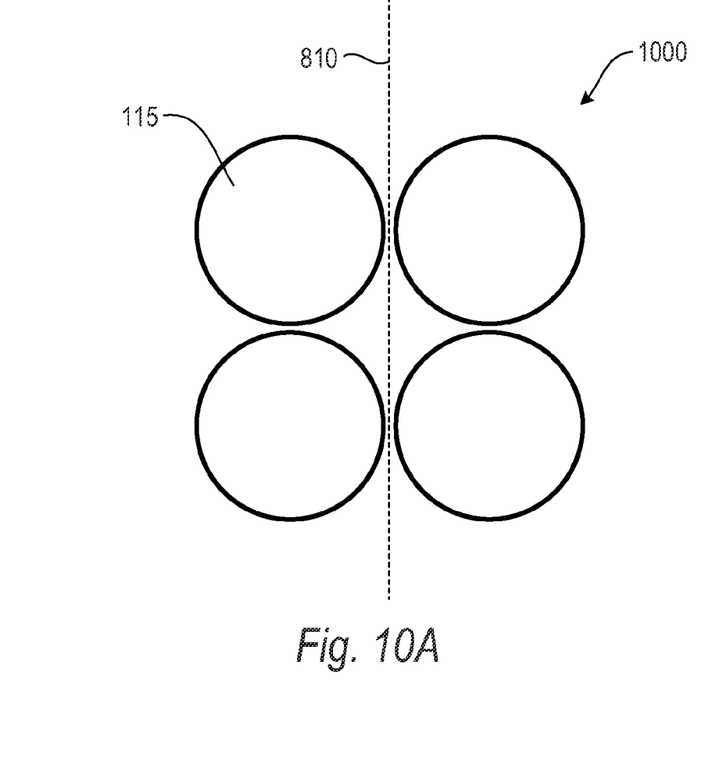
FIGS. 10A-10B are top plan views that depict, respectively, an example symmetrical nanostructure and an example lower symmetry nanostructure, as described herein but without supporting structures, wherein the lower symmetry of the less symmetric nanostructure is due to a lack of inversion symmetry.
Figure 10B:
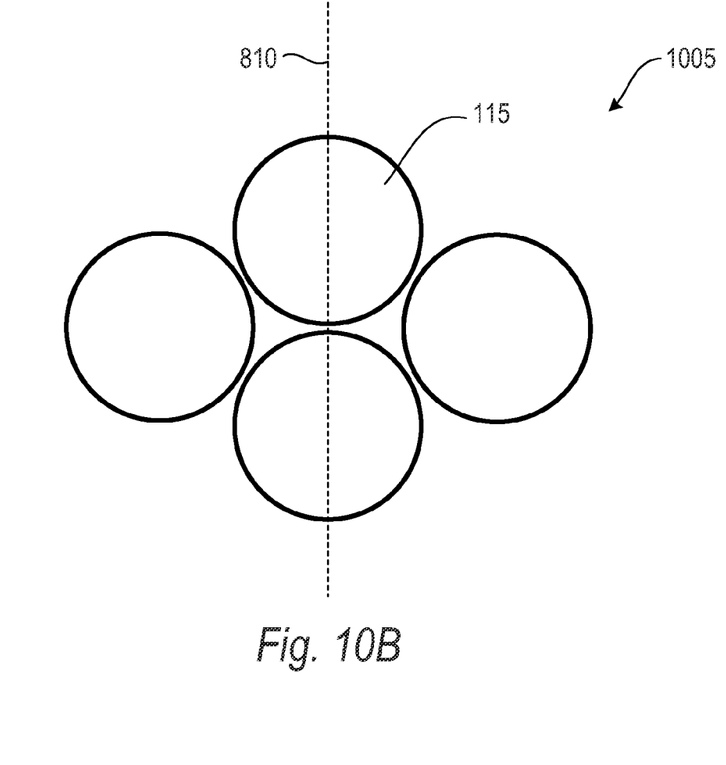

FIGS. 10A-10B are top plan views that depict, respectively, an example symmetrical nanostructure and an example less-symmetrical nanostructure, as described herein but without supporting structures, wherein the decrease in symmetry of the latter nanostructure is due to a lack of inversion symmetry. FIG. 10A is an example of a symmetrical nanostructure 1000 including four nanofingers 115. As seen in FIG. 10A, a mirror plane of symmetry 810 can be drawn down the center of the nanostructure 1000. In contrast, FIG. 10B is an example of a less-symmetrical nanostructure 1005 including four nanofingers 115. While a mirror plane of symmetry 810 can be drawn down the center of the nanostructure 1005, the nanostructure 1005 lacks inversion symmetry.

In general, the hybrid nanostructure disclosed herein provides several advantages. For example, hybrid nanostructures can be fabricated using a method other than the restrictive top-down or bottom-up methods. Additionally, the hybrid nanostructures can be formed in different geometries, which may result in hybrid nanostructures having different and/or enhanced properties. In one example, by using nanoparticles with different diameters, the size of the finger gaps can be controlled on a nanometer scale, which may improve the Raman signal strength of analytes present on the hybrid nanostructure. In another example, a break in the symmetry of the hybrid nanostructure geometry, as described herein, may also improve the Raman signal strength of analytes present on the hybrid nanostructure. Finally, using hybrid nanostructures may provide for a new sensing method, where both the target-related Raman signals and the plasmonic resonance induced by the target-linked nanoparticles can be monitored.

What is claimed is:

1. A hybrid nanostructure for molecular analysis, the structure including:
    a plurality of nanofingers, wherein each nanofinger is coated with a metal coating layer that coats over the entire nanofinger and has a different chemical composition from the nanofinger, is attached at one end to a substrate, and is freely bendable along its length such that the second ends of each nanofinger are capable of movement toward each other to form a cavity; and
    a nanoparticle trapped in the cavity, wherein the nanoparticle includes a semiconducting material.

2. The hybrid nanostructure of claim 1 wherein the plurality of nanofingers and the nanoparticle are arranged symmetrically, less symmetrically or asymmetrically.

3. The hybrid nanostructure of claim 1 wherein an array of the hybrid nanostructures on the substrate is provided.

4. The hybrid nanostructure of claim 1 wherein the plurality of nanofingers includes a thermoplastic polymer, a curable material, or any combination thereof, and wherein one nanofinger in the plurality of nanofingers either has the same composition or has a different composition than another nanofinger in the plurality of nanofingers.

5. The hybrid nanostructure of claim 1 wherein the plurality of nanofingers includes an inorganic material selected from the group consisting of alumina, aluminum, copper, diamond, diamondlike carbon, germanium, silicon, silicon nitride, silicon oxide, and silicon oxynitride, and wherein one nanofinger in the plurality of nanofingers has the same composition or has a different composition than another nanofinger in the plurality of nanofingers.

6. The hybrid nanostructure of claim 1 wherein the metal coating layer includes a material that supports intense surface plasmons.

7. An array of hybrid nanostructures for molecular analysis,
wherein each hybrid nanostructure in the array includes the hybrid nanostructure of claim 1,
wherein the plurality of nanofingers in each hybrid nanostructure are either of the same height or of different heights as the plurality of nanofingers in other hybrid nanostructures, and wherein each nanofinger has a height between about 50 nm and 2 μm, a diameter between about 10 nm and 1 μm, and a spacing of between about 10 nm and 500 nm measured at the second ends of the plurality of nanofingers.

8. The array of claim 7 for molecular analysis in a surface-enhanced Raman spectroscopy (SERS) apparatus including a Raman-excitation light source and a photodetector, wherein the photodetector is on the same side of the substrate as the plurality of nanofingers, and wherein the light source is either on the same side of the substrate as the plurality of nanofingers or on the opposite side of the substrate from the plurality of nanofingers.

9. The array of claim 7 for molecular analysis using enhanced fluorescence, enhanced luminescence, optical scattering, optical absorption, or plasmonic sensing.

* * * * *